US006849404B2

(12) United States Patent
Park et al.

(10) Patent No.: US 6,849,404 B2
(45) Date of Patent: Feb. 1, 2005

(54) POLYMERASE CHAIN REACTION OF DNA OF WHICH BASE SEQUENCE IS COMPLETELY UNIDENTIFIED

(75) Inventors: Han Oh Park, Chungbuk (KR); Se-Yeon Weon, Taejon (KR); Joo-Won Rhee, Chungbuk (KR); In-Suk Joung, Chungbuk (KR); Su-Nam Song, Chungbuk (KR); Jin-Tae Jeon, Chungbuk (KR)

(73) Assignee: Bioneer Corporation, Choongcheongbuk-Do (KR)

( * ) Notice: Subject to any disclaimer, the term of this patent is extended or adjusted under 35 U.S.C. 154(b) by 0 days.

(21) Appl. No.: 09/849,597

(22) Filed: May 7, 2001

(65) Prior Publication Data

US 2002/0192769 A1 Dec. 19, 2002

(51) Int. Cl.$^7$ ............................ C12Q 1/68; C12P 19/34; C07H 21/04
(52) U.S. Cl. .................. 435/6; 435/91.2; 435/91.21; 536/24.2
(58) Field of Search ................... 435/6, 91.2, 91.21; 536/24.2, 23.1

(56) References Cited

U.S. PATENT DOCUMENTS 5,470,724 A * 11/1995 Ahern ...................... 435/91.2
5,508,169 A * 4/1996 Deugau et al. ................ 435/6
5,516,663 A * 5/1996 Backman et al. .......... 435/91.2
5,858,656 A * 1/1999 Deugau et al. ................ 435/6
5,994,068 A * 11/1999 Guilfoyle et al. ............... 435/6
6,228,999 B1   5/2001 Guilfoyle et al. .......... 536/22.1
6,383,754 B1 * 5/2002 Kaufman et al. ............... 435/6

OTHER PUBLICATIONS

Sambrook et al. Strategies for cDNA cloning and Generation of nested sets of deletion mutants. Molecular cloning. A laboratory mannual. $2^{nd}$ edition. p. 8.11–8.33 and 15.14–15.19, 1989.*
Riley J et al. A novel, rapid method for the isolation of terminal sequences from yeast artificial chromosome (YAC) clones. Nucleic Acids Res., vol. 18, No. 10, pp. 2887–2890, 1990.*
Padegimas et al. Adaptor ligation–based polymerase chain reaction–mediated walking. Analytical Biochemistry, vol. 260, pp. 149–153, 1998.*

* cited by examiner

Primary Examiner—Jehanne Sitton
Assistant Examiner—Prabha Chunduru
(74) Attorney, Agent, or Firm—Birch, Stewart, Kolasch & Birch, LLP

(57) ABSTRACT

The present invention relates to a process for amplifying DNA of an organism. More particularly, the present invention is directed to a process for amplifying DNA of an organism through Polymerase Chain Reaction(PCR) without any information regarding a primer needed for amplifying DNA of an organism.

12 Claims, 3 Drawing Sheets

FIG. 1 a.

```
     TA
   G     CAGTAGATGCTTGACGTGAGTAGACGTCAGAGTAATACGGCG-3'
   C     GTCATCTACGAACTGCACTCATCTGCAGTCTCATTATGCC-5'
     TA
``` b.

```
     TA
   G     AGTAGTCGTCAGTAGCAGTCGAAGTATGACGACTGTATCGAG-3'
         TCATCAGCAGTCATCGACAGCTTCATACTGCTGACATAGC-5'
     TA
```

FIG. 2 a. 5'-CAGTACGTGCTTGACGTGAGTAGAC-3' b. 5'-AGTAGTCGTCAGTAGCAGTCGAAGT-3'

FIG.3

|    | AA | AC | AG | AT | CA | CC | CG | CT | GA | GC | GG | GT | TA | TC | TG | TT |
|----|----|----|----|----|----|----|----|----|----|----|----|----|----|----|----|----|
| AA |    | ▓  | ▓  | ▓  | ▓  | ▓  | ▓  | ▓  | ▓  | ▓  | ▓  | ▓  | ▓  | ▓  | ▓  | ▓  |
| AC |    |    | ▓  | ▓  | ▓  | ▓  | ▓  | ▓  | ▓  | ▓  | ▓  | ▓  | ▓  | ▓  | ▓  | ▓  |
| AG |    |    |    | ▓  | ▓  | ▓  | ▓  | ▓  | ▓  | ▓  | ▓  | ▓  | ▓  | ▓  | ▓  | ▓  |
| AT |    |    |    |    | ▓  | ▓  | ▓  | ▓  | ▓  | ▓  | ▓  | ▓  | ▓  | ▓  | ▓  | ▓  |
| CA |    |    |    |    |    | ▓  | ▓  | ▓  | ▓  | ▓  | ▓  | ▓  | ▓  | ▓  | ▓  | ▓  |
| CC |    |    |    |    |    |    | ▓  | ▓  | ▓  | ▓  | ▓  | ▓  | ▓  | ▓  | ▓  | ▓  |
| CG |    |    |    |    |    |    |    | ▓  | ▓  | ▓  | ▓  | ▓  | ▓  | ▓  | ▓  | ▓  |
| CG |    |    |    |    |    |    |    |    | ▓  | ▓  | ▓  | ▓  | ▓  | ▓  | ▓  | ▓  |
| GA |    |    |    |    |    |    |    |    |    | ▓  | ▓  | ▓  | ▓  | ▓  | ▓  | ▓  |
| GC |    |    |    |    |    |    |    |    |    |    | ▓  | ▓  | ▓  | ▓  | ▓  | ▓  |
| GG |    |    |    |    |    |    |    |    |    |    |    | ▓  | ▓  | ▓  | ▓  | ▓  |
| GT |    |    |    |    |    |    |    |    |    |    |    |    | ▓  | ▓  | ▓  | ▓  |
| TA |    |    |    |    |    |    |    |    |    |    |    |    |    | ▓  | ▓  | ▓  |
| TC |    |    |    |    |    |    |    |    |    |    |    |    |    |    | ▓  | ▓  |
| TG |    |    |    |    |    |    |    |    |    |    |    |    |    |    |    | ▓  |
| TT |    |    |    |    |    |    |    |    |    |    |    |    |    |    |    |    | ved
POLYMERASE CHAIN REACTION OF DNA OF WHICH BASE SEQUENCE IS COMPLETELY UNIDENTIFIED

TECHNICAL FIELD

The present invention generally relates to a process for amplifying DNA of an organism. More particularly, the present invention is directed to a process for amplifying DNA of an organism through Polymerase Chain Reaction (PCR) without any information regarding a primer needed for amplifying DNA of an organism.

BACKGROUND ART

The DNA contained in an organism and the mRNA transcribed from DNA, are very complex and small in amount. Therefore, amplification process is required for DNA analysis of the DNA sequence except few cases. Two kinds of techniques are generally used for this sequencing purpose.

In the first method, a DNA is selectively cloned in a microorganism or prepared to a library, and then after proliferation of the microorganism in a large scale, the microorganisms containing desired DNA fragments are isolated.

The second method is that desired DNA site is amplified by the Polymerase Chain Reaction (hereinafter, PCR). In the second method, however, there is a problem that the sequence of both ends of the desired DNA site should be noted in advance. Therefore, in case the base sequence of the DNA to be amplified has not yet been identified, the perfect amplification of full length DNA or cDNA of an organism through PCR process without missing any part thereof is impossible.

Generally, in order to analyze the base sequence of DNA in a large scale, a full length DNA of an organism is divided into several short fragments to be inserted into a vehicle for amplification, and then the base sequence of the DNA fragments thus amplified, are determined.

For this process, the ordered library is generally used. However, the ordered library technique is very difficult, complex, time-consuming and very laborious process, thus this process is the biggest obstacles for analyzing the DNA sequence.

Therefore, the object of the present invention is to provide a method for amplifying DNA without any information for the base sequence of the DNA to be amplified in advance.

DISCLOSURE OF THE INVENTION

The object of the present invention may be achieved by providing a process for digesting DNA into several fragments by using a restriction enzyme, ligating the fragments with adaptors which have a hairpin loop, removing the DNA fragments and adaptors which have not participated in ligation reaction by using an exonuclease, eliminating the hairpin loop by using an alkaline solution, an RNase or single strand specific exonuclease, and amplifying the DNA fragments by using a primer which can combine complementarily to a residual sequence from the adapters.

The process of the present invention comprises:

i) digesting DNA into several fragments which have single-strand cohesive ends by using a restriction enzyme, and separately from the above, ii) preparing hairpin loop adaptors which have the single-strand cohesive ends which can be complementarily combined to and ligated on both ends of the DNA fragments obtained in the above;

iii) ligating the DNA fragments with the hairpin loop adapters prepared in step ii) by using a DNA ligase;

iv) removing DNA fragments and hairpin loop adapters which have not participated in the ligation reaction by using an exonuclease;

iv) optionally, eliminating a hairpin loop by using an alkaline solution, an RNase or a single strand specific exonuclease; and v) amplifying the DNA fragments by using a DNA polymerase and a primer which can combine complementarily to a residual sequence from the adapters, thereby obtaining a DNA in a large amount through Polymerase Chain Reaction from DNA of which sequence is completely unidentified.

In addition, another object of the present invention can achieved by providing a process for preparing a library of DNA fragments of which terminal sequence are known by using a DNA of which base sequence is completely unidentified, which comprises:

i) digesting a DNA into fragments which have single-strand cohesive end by using a restriction enzyme, and separately from the above, ii) preparing a series of hairpin loop adapters which have single-strand cohesive ends of which base sequence is known;

iii) ligating the DNA fragments with the hairpin loop adapters prepared in the above step ii) by using a DNA ligase;

iv) eliminating a hairpin loop only from the DNA fragments which contain hairpin loop adapters, obtained in step iii) by using an alkaline solution, an RNase or a single strand specific exonuclease.

Yet another object of the present invention is to provide a series of hairpin loop adapters which have single-stand cohesive ends, which comprise hairpin loop adapters of which single-stand cohesive ends comprising all sorts of single-strand DNAs which can be made by a random combination of four (4) nucleotides.

Hereinafter, the process of the present invention, the DNA fragments, hairpin loop adapters, a restriction enzyme and primers of the present invention will be explained in more detail.

The adapter which has a hairpin loop structure, illustrated in FIG. 1, is distributed in the test tubes which are arranged according to FIG. 3 by following methods. For example, as illustrated in the FIG. 3, in case CG is located in column 7 and AG is located in row 3, adapters which contain CG in the terminal of cohesive end (for column) and adapters contain AG in the terminal of cohesive end (for row) are mixed.

In case where the number of nucleotides which constitute the single-strand cohesive end, is two, the number of test tubes of the arrangement, are 112. In case where the number of nucleotides which constitute the cohesive end is N, the number of a kind of hairpin loop adapter, is $(4^{2n}-2*4^n)/2$. The 5', 3' terminals of an adapter and those of DNA fragments should be combined complementarily.

After distributing the hairpin loop adapters into each test tube in the above mentioned way, DNA fragments obtained by using restriction enzymes, are mixed in the test tubes with appropriate amounts. Then, ligation reaction is performed.

After the ligation reaction, the DNA fragments and hairpin loop adapters which have not participated in the ligation reaction are removed by adding an exonuclease to each test tube. Then, DNA fragments which have a hairpin loop in the ends, remain without any damage from the exonuclease attacks.

The hairpin loop may be eliminated by treatment of an alkaline compound, such as, NaOH or by using an RNase or a single strand specific exonuclease, to produce a normal DNA double strand.

PCR is performed with the primer which can complementarily combine to the terminal sequence of DNA obtained in the above, which originated from the adapter and remains on the DNA after the elimination of hairpin loop.

PCR products thus obtained may be separated through polyacrylamide gel electrophoresis, and DNA obtained from each band of gel may be used for further analysis.

The above process may be performed repeatedly by using another restriction enzymes. A full length DNA of an organism may be analyzed by comparing the nucleotide sequences obtained by using various restriction enzymes. In case of mRNA, in principle, the sequence of all kinds of mRNA of an organism, may be determined through the process of the present invention.

BRIEF DESCRIPTION OF THE DRAWINGS

The above objects and other advantages of the present invention will become more apparent by describing in detail the examples thereof with reference to the attached drawings, in which:

FIG. 1 is an example of the hairpin-structured adapter which is used for column (a) (SEQ ID NO: 1) or row (b)(SEQ ID NO: 2) of the arrangement (herein, rN refers to ribonucleotide or deoxyribonucleotide which can make loop shape, and others refer to each nucleotide of DNA).

FIG. 2 is an example of the sequence of primers (SEQ ID NOS 3 & 4) for PCR and nucleotide sequence analysis, which is used for the adapter contained in test tubes column (a) or row (b) of the arrangement.

FIG. 3 is an example of 16×16 test tubes arrangement used in ligation reaction, exonuclease reaction, RNA or loop DNA lysis reaction, and polymerize chain reaction (herein, the AA and the like represent the nucleotide sequence of the terminal of cohesive end in DNA/RNA hairpin loop adapter contained in each test tube of the arrangement).

Figure 4:
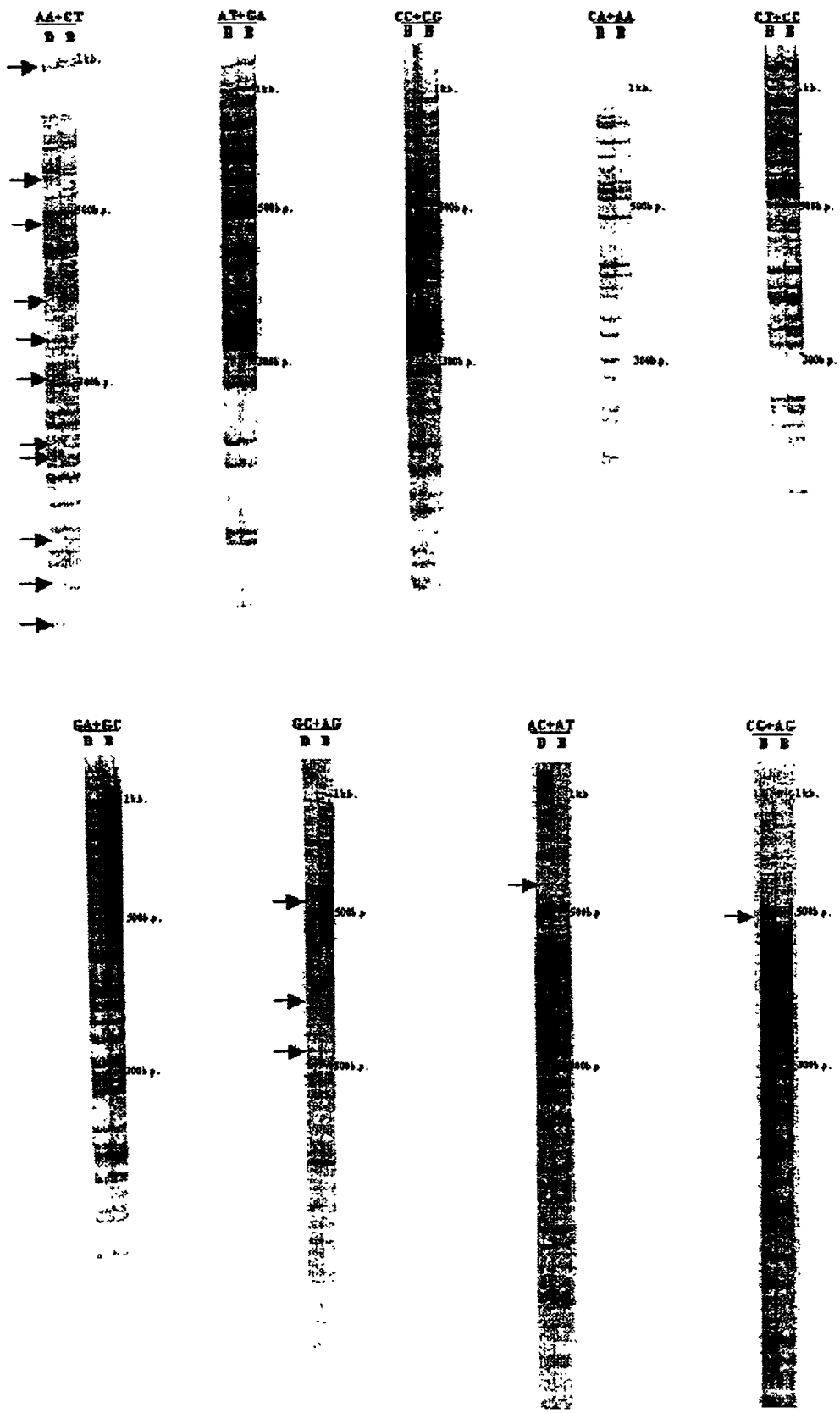
FIG. 4 is the photographs of the bands developed by the silver staining method, and of the DNA fragments separated by electrophoresis (herein, AT+GA and the like represent combinations of the base sequence of the cohesive ends of the hairpin adaptor and the number indicated in right of DNA band in right represent the relative size of DNA band. The black arrow represent the difference of the fragments in two kinds of E. coli.)

EXAMPLE 1
Method for Selective Amplification of E. coli Genome

1) Fragmentation of E. coli genome by using an Hpy118III restriction enzyme of IIs type.

Whole genomes were separated from E. coli strain DH5a and BL21 respectively. 30 units of Hpy118III restriction enzyme were put into 10 µg of each genomes thus separated, the mixture thus obtained was added into buffer solution in pH 7.9 which contains 50 mM of acetic potassium, 20 mM of tris-acetate, 10 mM of magnesium nitrate and 1 mM of DTT to proceed the restriction enzyme reaction.

1—1) Fragmentation of E. coli genome by using an Hpy118III restriction enzyme of IIs type.

Whole genomes were separated from E. coli strain DH5a and BL21 respectively. 30 units of Hpy118III restriction enzyme were put into 10 µg of each genomes thus separated, the mixture thus obtained was added into buffer solution in pH 7.9 which contains 50mM of acetic potassium, 20 mM of tris-acetate, 10 mM of magnesium nitrate and 1 mM of DTT to proceed the restriction enzyme reaction.

2) ligation DNA fragment and hairpin loop adapter. Each DNA fragments obtained by using restriction enzyme in step 1) was purified with Accuprep™ PCR purification KIT (manufactured by Bioneer corporation). 1 µg of the DNA fragments obtained from the above, was diluted in the buffer solution containing 50 mM of Tris-HCl, 10 mM of MgCl2, 5 mM of DTT, 2 mM of ATP, 25 mg/Ml of BSA, and then 2 µM of hairpin adaptors and 1 unit of T4 DNA ligase was added into the mixture prepared in the above, and selective ligation reaction was proceeded at the total volume of 50 µl. In this example, nine pairs of AT+GA, CC+CG, CA+AA, CT+CC, GA+GC, AG+CA, GC+AC, AC+AT, CG+AG were used, which illustrated in columns and a rows of FIG. 3 are used.

3) Elimination of DNA fragments and adaptors not ligated by using Exonuclease III:

5 µg of the product of the above step was put into a buffer solution containing 500 mM of Tris-HCl(pH 8.0), 50 mM MgCl2 and 100 mM 2-Mercaptoethanol, and then 20 units of exonuclease III was added into the reaction mixture obtained in the above, to make 30 µl of the total volume. The elimination reaction was carried out at 37° C. for 45 minutes.

4) Amplification reaction by polymerase chain reaction

3 µl of DNA ligated with adapter in step 2) and 3), a template, and each 1 µM of a primer for a column and a primer for a row illustrated in FIG. 2 were added into the mixture of 100 mM Tris-HCl(pH 8.3), 400 mM KCl, 15 mM MgCl2, 10 mM DTT, 5 µg/µl acetylated BSA and Taq DNA polymerase 1 unit to make total volume of 20 µl. Then Polymerase Chain Reaction was proceeded for one(1) time at 94° C. for 5 minutes, at 55° C. for 35 seconds, and 72° C. for 2 minutes, and 30 times at 94° C. for 35 seconds, at 55° C. for 35 seconds and 72° C. for 2 minutes, one time at 94° C. for 35 seconds and 55° C. for 35 seconds and 72° C. for 5 minutes.

5) Separation of DNA fragments in polyacrylamide gel by silver staining method.

10 µl of DNA fragments obtained in step 4) was separated by electrophoresis through 4% polyacrylamide/urea gels. The gel thus obtained was with 10% of acetic acid solution (fixation solution) for 30 minutes. Thereafter, the gels were washed three times with distilled water. The gels were stained in 1 l solution containing 1 g of AgNO3 and 1.5 Ml of 37% formaldehyde for 30 minutes. The stained gels were washed with deionized water for 5 seconds, and then were stained in a developing solution (1□ solution containing 40 g of sodium carbonate, 1.5 Ml of 37% formaldehyde, 200 µl of sodium thiosulfate(10 mg/Ml)) at 4° C., And then the gels thus treated, were reacted with fixative solution for 5 minutes, and were washed with distilled water for 10 minutes. The results are shown in FIG. 4. In FIG. 4, AT+GA and the like represent combinations of the base sequence of the cohesive ends of the hairpin adaptor and the number indicated in right of DNA band in right represent the relative size of DNA band. The black arrow represent the difference of the fragments in two kinds of E. coli.

The reaction conditions of the above examples are as follows:

1. Genomic DNA preparation of *E. coli* DH5a and *E. coli* BL21 (ref.: pp. 2.4 Fred Ausubel et. al. Short protocols in molecular biology 3rd edition)
2. Digestion of genomic DNA with restriction endonuclease

| | |
   |---|---|
   | genomic DNA | 10 ug |
   | restriction endonuclease(Hpy118III) | 30 unit |
   | 10X reaction buffer | 50 uL |
   | d.d.w | up to 500 uL |

Overnight incubation at 37° C.
3. Ligation of genomic DNA fragments and hair pin adaptors

| | |
   |---|---|
   | genomic DNA | 1 ug |
   | A hair pin adaptor | 100 pmole |
   | B hair pin adaptor | 100 pmole |
   | 10X ligation buffer | 50 uL |
   | Ligase | 1 unit |
   | d.d.w | up to 50 uL |

1 hour incubation at room temperature
4. Digestion of unligated DNA with Exonuclease III

| | |
   |---|---|
   | ligation mix | 5 uL |
   | Exonuclease III reaction buffer | 3 uL |
   | Exonuclease III | 20 unit |
   | d.d.w. | up to 30 uL |

45 minute incubation at 37° C.
5. PCR amplification of the ligated DNA

| | |
   |---|---|
   | ExoucleaseIII digestion mix (template) | 3 uL |
   | A-PCR primer | 20 pmole |
   | B-PCR primer | 20 pmole |
   | 10X reaction buffer | 2 uL |
   | 10X dNTP mix | 2 uL |
   | Taq DNA polymerase | 1 unit |

1 cycle of 94° C. 5 minute, 55° C. 35 second and 72° C. 2 minute 30-cycle of 94° C. 35 second, 55° C. 35 second and 72° C. 2 minute 1 cycle of 94° C. 35 second, 55° C. 35 second and 72° C. 5 minute
6. Display in polyacrylamide gel
   4% denaturing polyacrylamide gel in TBE solution
   37.5 Volt/cm
   80 minute running
   silver staining Based on the above, the average size of DNA fragments indicated by the band was about 400 base pairs. The average number of band obtained from one(1) ligation reaction was about 110. In case of performing 120 ligation reactions according to the present process, DNA of 5.28 mega b.p which exceeds the size of whole genomic DNA of *E. coli*(4.72 mega b.p) can be obtained. As illustrated in FIG. 4, 11 distinct bands in AA+CT pair, 3 distinct bands in GG+AG pair, and 1 distinct bands in AC+AT and CG+AG pairs, respectively, were confirmed.

About 5,000 b.p of sequence is different from each other between *E. coli* DH5α and *E. coli* BL21. If all of the reactions of these examples were performed, about 7200 b.p of sequence can be confirmed and thus, conclusively, all DNA sequences different from each other between genomic DNAs of two kind variation, could be confirmed through the process of the present invention

INDUSTRIAL APPLICABILITY

As described in the above, through the process of the present invention, a full length DNA of an organism, of which sequence is completely unknown, can be entirely amplified by means of PCR. Therefore, single nucleotide polymorphism in the nucleotide sequence of each individual variation can be analyzed easily by the process of the present invention.

While the present invention has been particularly shown and described with reference to particular embodiment thereof, it will be understood by those skilled in the art that various changes in form and details may be effected therein without departing from the sprit and scope of the invention as defined by the appended claims.

What is claimed is:

1. A process for preparing a library of DNA fragments of which terminal sequences are known by using a DNA of which base sequence is completely unidentified, which comprises:
   i) digesting a DNA into fragments which have single-strand cohesive ends by using a restriction enzyme,
   ii) preparing a series of hairpin loop adapters which have single-strand cohesive ends of which base sequence is known;
   iii) ligating the DNA fragments with the hairpin loop adapters prepared in the above step ii) by using a DNA ligase;
   iv) removing DNA fragments and hairpin loop adapters which have not participated in the ligation reaction by using an exonuclease; and
   (v) eliminating a hair pin loop structure only from the DNA fragments which contain the hairpin loop adapters, obtained in step iii), by using an alkaline solution, am RNase or a single strand specific exonuclease.

2. A process for selective amplifying DNA of which base sequence is completely unidentified, which comprises:
   i) digesting a DNA into fragments which have a single-strand cohesive end group by using a restriction enzyme,
   ii) preparing hairpin loop adaptors which have the single-strand cohesive end which can be complementarily combined to and ligated on the both ends of the DNA fragments obtained in step i);
   iii) ligating the DNA fragments with the hairpin loop adapters thus prepared by using a DNA ligase;
   iv) removing DNA fragments and hairpin loop adapters which have not participated in the ligation reaction by using an exonuclease;
   v) eliminating a hairpin loop structure from the DNA fragments on which said hairpin loop adapters are ligated in step iii); and
   vi) amplifying the DNA fragments by using a DNA polymerase and a primer which can combine complementarily to a residual sequence from the adapters.

3. The process according to claim 2, wherein the restriction enzyme is type IIs restriction enzyme.

4. The process according to claim 2, wherein the restriction enzyme is type hip restriction enzyme.

5. The process according to claim 2, wherein the DNA ligase in step iii) is T4 DNA ligase.

6. The process according to claim 2, wherein the exonuclease in step iv) is exonuclease III.

7. The process according to claim 2, wherein the hairpin loop is eliminated by using alkaline solution.

8. The process according to claim 2, wherein the hairpin loop is eliminated by using RNase.

9. The process according to claim 2, wherein the hairpin loop is eliminated by using single strand specific exonuclease.

10. The process according to claim 2, wherein the DNA Polymerase is Taq DNA polymerase.

11. The method according to claim 1, wherein the series of hairpin loop adapters have a single-stand cohesive end comprising all sorts of single-strand DNAs which can be obtained by a random combination of four (4) nucleotides.

12. The method according to claim 2, wherein the series of hairpin loop adapters have a single-stand cohesive end comprising all sorts of single-strand DNAs which can be obtained by a random combination of four (4) nucleotides.

* * * * *

SEQUENCE LISTING

```
<160> NUMBER OF SEQ ID NOS: 4

<210> SEQ ID NO 1
<211> LENGTH: 88
<212> TYPE: DNA
<213> ORGANISM: Unknown Organism
<220> FEATURE:
<223> OTHER INFORMATION: Description of Unknown Organism: Unknown hair-
      pin structured adapter

<400> SEQUENCE: 1
ccgtattact ctgacgtcta ctcacgtcaa gcatctactg atcgtacagt agatgcttga      60
cgtgagtaga cgtcagagta atacggcg                                        88

<210> SEQ ID NO 2
<211> LENGTH: 87
<212> TYPE: DNA
<213> ORGANISM: Unknown Organism
<220> FEATURE:
<223> OTHER INFORMATION: Description of Unknown Organism: Unknown hair-
      pin structured adapter

<400> SEQUENCE: 2
cgatacagtc gtcatacttc gacagctact gacgactact atgtaagtag tcgtcagtag      60
cagtcgaagt atgacgactg tatcgag                                         87
```

-continued

```
<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
cagtacgtgc ttgacgtgag tagac                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
agtagtcgtc agtagcagtc gaagt                                          25
```